(12) United States Patent
Blaber et al.

(10) Patent No.: US 7,790,682 B1
(45) Date of Patent: Sep. 7, 2010

(54) ENGINEERED HUMAN ACIDIC FIBROBLAST GROWTH FACTORS AND ASSOCIATED METHODS

(75) Inventors: Michael Blaber, Tallahassee, FL (US); Stephen R. Brych, Simi Valley, CA (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 68 days.

(21) Appl. No.: 11/001,804

(22) Filed: Dec. 2, 2004

Related U.S. Application Data (60) Provisional application No. 60/526,428, filed on Dec. 2, 2003.

(51) Int. Cl.
  *C12P 21/06* (2006.01)
  *C12N 15/00* (2006.01)
  *C12N 5/00* (2006.01)
  *A61K 38/18* (2006.01)
  *C07H 21/04* (2006.01)

(52) U.S. Cl. .................. 514/12; 536/23.5; 435/69.1; 435/320.1; 435/325

(58) Field of Classification Search .................. None
  See application file for complete search history.

(56) References Cited

U.S. PATENT DOCUMENTS 5,491,220 A * 2/1996 Seddon et al. .............. 530/399
6,294,359 B1 * 9/2001 Fiddes et al. ............... 435/69.4

OTHER PUBLICATIONS

Brych et al., Protein Science, 12:2704-2718, Dec. 2003.*
Brych et al., Journal of Molecular Biology, 344:769-780, Nov. 2004.*

* cited by examiner

*Primary Examiner*—Marianne P Allen
(74) *Attorney, Agent, or Firm*—Allen, Dyer, Doppelt, Milbrath & Gilchrist, P.A.

(57) ABSTRACT

An engineered, purified polypeptide of acidic fibroblast growth factor (FGF-1) is described, the amino acid sequence of which consists essentially of SEQ ID NO: 1. The engineered polypeptide provides 70 times the mitogenic activity of wild type acidic fibroblast growth factor. Other engineered FGFs are also described, having altered properties, including reduced heparin binding affinity and increased mitogenicity as demonstrated with a model mammalian cell line derived from mice, NIH 3T3 fibroblasts.

7 Claims, 5 Drawing Sheets

ENGINEERED HUMAN ACIDIC FIBROBLAST GROWTH FACTORS AND ASSOCIATED METHODS

RELATED APPLICATION

This application claims priority from provisional application Ser. No. 60/526,428, which was filed on Dec. 2, 2003, and which is incorporated herein by reference in its entirety.

FIELD OF THE INVENTION

The present invention relates to the field of mammalian tissue growth factors and, more particularly, to polypeptides comprising engineered mutants of acidic fibroblast growth factor which demonstrate altered biological activity.

BACKGROUND OF THE INVENTION

Analysis of the structural databank indicates that the overwhelming majority of protein structures can be classified as belonging to one of a very limited number of fundamental protein architectures (currently comprising ten such "superfolds"). These architectures represent a kinetic and thermodynamic solution to the protein folding problem, and their limited number suggests that the evolution of functionality within the proteome is achieved primarily through modification of existing protein architectures, rather than entirely new designs. Experimental and theoretical studies of protein stability and function relationships suggest that novel functionality is typically achieved at the expense of stability (i.e. the "stability/function tradeoff" hypothesis). Together, these results additionally suggest that an important property of the ten fundamental superfolds is the ability to accommodate a wide variety of mutations, yet remain stably folded. Thus, the ten fundamental protein architectures likely share a basic property, namely, the potential for substantial thermodynamic stability.

The majority of the fundamental superfolds exhibit some form of tertiary structure symmetry, the postulated result of gene duplication and fusion events during the evolutionary process. Despite this tertiary structure symmetry, such proteins may exhibit little if any related primary structure symmetry, indicating substantial divergence must have occurred following the presumed ancient gene duplication/fusion events. Based upon the stability/function trade-off hypothesis, some fraction of the observed divergence is associated with the emergence of novel functionalities, but at the expense of stability. This leads to the intriguing hypothesis that it may be possible to redesign a protein, belonging to a symmetric superfold, by enforcing a symmetric primary structure constraint, and yet, have the resulting mutant protein increase thermodynamic stability. Such design solutions would have obvious importance in elucidating the process of protein evolution, and also have practical applications in de novo protein design.

SUMMARY OF THE INVENTION

With the foregoing in mind, the present invention advantageously provides various engineered polypeptides of acidic fibroblast growth factor (FGF) having altered biological activities, for example, increased mitogenic activity and decreased heparin binding affinity.

The various FGF-1 polypeptides are identified herein by their amino acid sequences and their designations, as follows: SEQ ID NO: 1 is an engineered mutant polypeptide according to the present invention and is also designated SYM6ΔΔ or SYM6DD, the symbols "Δ" and "D" referring to one or more deletions which may additionally be identified by their position, for example, 120-122. SEQ ID NO: 2 is an engineered mutant polypeptide according to the present invention and is also designated SYM5Δ120-122 or SYM5D120-122. SEQ ID NO: 3 is also an engineered mutant polypeptide according to the present invention and is designated WTΔ120-122 or WTD120-122; and SEQ ID NO: 4 is the wild type polypeptide for FGF-1, also designated acidic fibroblast growth factor, WT*, or WT FGF-1. The various fibroblast growth factors are designated generically as a group as FGFs.

In previous studies designed to increase the primary structure symmetry within the hydrophobic core of acidic fibroblast growth factor (FGF-1) five mutations were accommodated, resulting in structure, stability and folding kinetic properties similar to wild type, despite the symmetric constraint upon the set of core residues. A sixth mutation in the core, involving a highly-conserved Met residue at position 67, appeared intolerant to substitution. Structural analysis suggested that the local packing environment of position 67 involved two regions of apparent insertions that distorted the tertiary structure symmetry inherent in the β-trefoil architecture.

We postulated that a symmetric constraint upon the primary structure within the core could only be achieved after these insertions had been deleted, which we expected to result in concomitantly increasing the tertiary structure symmetry. We have now shown that the deletion of these insertions permits mutation of position 67, thereby increasing the primary structure symmetry relationship within the core. Furthermore, despite the imposed symmetric constraint upon both the primary and tertiary structure, the resulting mutant form of FGF-1 is substantially more stable.

The apparent inserted regions are shown to be associated with heparin-binding functionality, however, despite a marked reduction in heparin-binding affinity the preferred mutant form of FGF-1 herein disclosed is surprisingly ~70 times more potent in 3T3 fibroblast mitogenic assays. These unexpected results support the hypothesis that primary structure symmetry within a symmetric protein superfold represents a possible solution, rather than a constraint, to achieving a foldable polypeptide.

Figure 1:
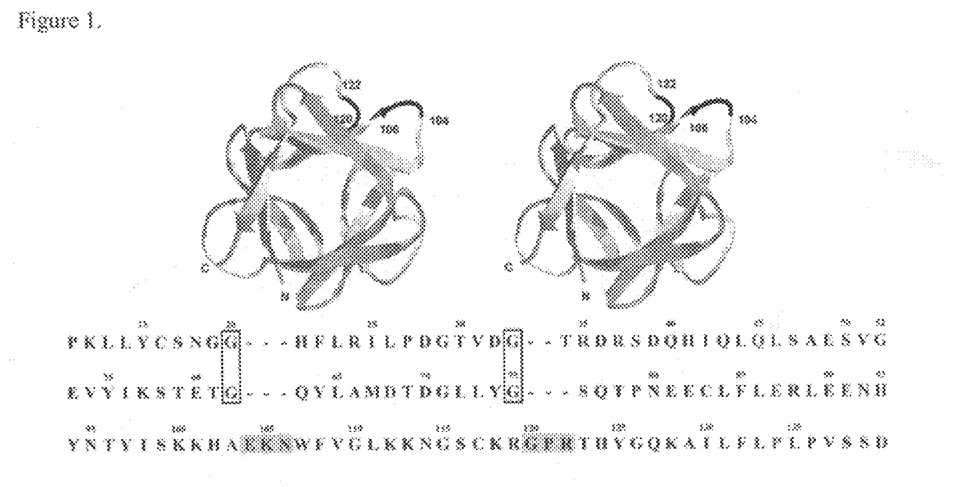
FIG. 1 is a ribbon diagram of a polypeptide, wherein the upper panel shows a relaxed stereo ribbon diagram of wild-type FGF-1 (SEQ ID NO: 4; PDB accession 2AFG) oriented down the three-fold axis of symmetry, and with the locations of the loop deletions indicated; the amino and carboxyl termini are also indicated; and wherein the lower panel shows the amino acid sequence alignment (using the single-letter code) of residues 11-140 for the three trefoil subdomains in FGF-1; shaded residues indicate the locations of the loop deletions in the third domain; and the boxed residues indicate Gly amino acids located at the i+3 position in local β-turn secondary structure.

Human acidic fibroblast growth factor (FGF-1), one of 23 known polypeptides of the FGF family, is a member of the β-trefoil superfold and exhibits a characteristic three-fold tertiary structure symmetry, as illustrated in FIG. 1. However, as is often the case, this structural symmetry does not extend to the level of the primary structure, which is marginally above random identity when comparing the symmetry-related structural subdomains (FIG. 1). In previous reports we have investigated the structural, thermodynamic and kinetic consequences of redesigning the hydrophobic core region with the imposition of a three-fold symmetric constraint upon the primary structure. These results show that an alternative core packing group could be identified that exhibited similar kinetic and thermodynamic properties as wild type. Although no more stable than wild type, it was nonetheless striking that the core could be efficiently repacked despite the three-fold symmetric constraint upon the primary structure.

This alternative core did not, however, involve the entire set of 15 core residues. In particular, we previously found that position 67 (a Met residue) appeared intolerant to substitution (e.g. $\Delta\Delta G$ for Met67$\Rightarrow$Ile was +9.4 kJ/mol, although the other two symmetry-related positions could readily adopt an Ile side chain). Here $\Delta G$ is referring to the free energy of unfolding (a measure of stability) for a protein, and $\Delta\Delta G$ is referring to the change in that free energy for a mutation (in reference to the wild type value). Positive values mean the mutant is less stable than the wild type protein. This Met side chain, which is conserved in 22 of the 23 members of the FGF family, was observed to pack against two adjacent loop structures. Both these loops, in relationship to their three-fold symmetry mates, contained insertions within their primary structures, the insertions involving residue positions 104-106 and 120-122; as illustrated in FIG. 1. These insertions, and their local packing interactions, were postulated as the structural basis for the requirement of the invariant Met at position 67. It was further postulated that if the insertions within these two loops were deleted, that position 67 would exhibit a structural environment similar to its three-fold symmetry mates, and might therefore accommodate an Ile side chain. However, it was noted that these loops had functions attributed to them; the loop involving residues 104-106 was a reported low-affinity receptor binding site, and the loop involving residues 120-122 was part of a heparin-binding site. Thus, while the proposed loop deletions would increase the structural symmetry of the polypeptide, they were expected to simultaneously reduce the activity of specific functionalities.

Herein we describe the biophysical and functional analysis of deletion mutations within the two loops that surround the Met residue at position 67, in combination with an Ile mutation at this position. The results show that the interactions between the loop deletion mutations and position 67 substitution mutation are highly cooperative and the combination of all three increases the protein stability by a substantial 16.1 kJ/mol. The biophysical characterization of the combination mutant (SYM6ΔΔ; SEQ ID NO: 1) indicates that the heparin-binding affinity has been markedly reduced. Surprisingly, however, this combination mutant exhibits ~70 times greater mitogenic potency in comparison to the wild type polypeptide (SEQ ID NO: 4).

The background form of FGF-1 used as a starting point for the presently described engineered polypeptides is the previously reported "SYM5" highly-symmetric core mutant form of FGF-1 (involving five point mutations, as listed in Table I). Thus, the final and most preferred mutagenized form of FGF-1 resulting from the current study (SYM6ΔΔ; SEQ ID NO: 1) is the most symmetric (at both the tertiary and primary structure level) form of FGF-1 produced to date, involving a total of eight substituted positions combined with six deleted positions.

The results therefore provide support for the postulate that a symmetric primary structure within a symmetric protein superfold represents a possible solution to the problem of achieving a highly thermostable folded polypeptide, derivable from gene duplication/fusion events, and useful for subsequent diverse functional adaptive radiation. In addition, such novel polypeptide structures may concurrently exhibit unexpectedly altered biological functionalities.

BRIEF DESCRIPTION OF THE DRAWINGS

Some of the features, advantages, and benefits of the present invention having been stated, others will become apparent as the description proceeds when taken in conjunction with the accompanying drawings, presented solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, technical and scientific terms used herein have the same meaning as commonly understood by those of ordinary skill in the art to which this invention pertains. Although methods and materials similar or equivalent to those described herein can be used in the practice or testing of the present invention, suitable methods and materials are described below. A disclosure of the present invention was accepted on Sep. 21, 2004, for publication in Journal of Molecular Biology and has been available online through the web site for Sciencedirect. This and any other publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided solely for exemplary purposes so that this disclosure will be thorough and complete, and will fully convey the scope of the invention to those skilled in the art. Other features and advantages of the invention will be apparent from the following detailed description, and from the claims.

Materials and Methods

Design of Mutations.

Figure 2:
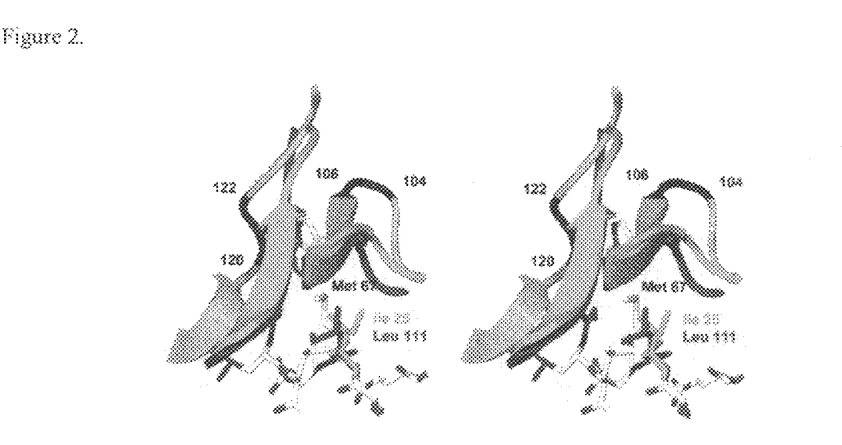
FIG. 2 shows a relaxed stereo image of WT* FGF-1 (PDB accession 1JQZ) in the vicinity of Met 67 (CPK colored wireframe representation) with the local loop structures (grey ribbon representation) and indicating the locations of residues 104-106 and 120-122 (deleted regions in the Δ104-106 and Δ120-122 mutations; dark ribbon shading); overlaid with this are the regions surrounding the symmetry-related positions Ile 25 (green color) and Leu 111 (blue color) in WT* FGF-1.

A prior structural and mutational analysis of a conserved Met residue at position 67 in FGF-1 indicated that it was intolerant of substitution and also resided within a unique packing environment that was not conserved at the three-fold symmetry-related positions of Ile 25 and Leu 111. The local packing environment of Met 67 includes two regions of apparent insertions, involving residue positions 104-106 and 120-122, in comparison to the symmetry-related positions (FIGS. 1 and 2). Deletion of these insertions was postulated to be a structural precondition to permit successful mutation of the Met 67 residue. However, deletion was also postulated to result in the formation of adjacent β-turn structures, with a requirement of a Gly residue at positions 103 22 and 119, respectively.

The 104-106 deletion disclosed herein thus includes an Ala103⟹Gly substitution mutation, and the 120-122 deletion mutation includes an Arg119⟹Gly substitution mutation. For brevity, the nomenclature for these deletion mutations is simply "Δ104-106", and "Δ120-122", respectively (see also Table I). The combination of both deletion mutations is referred to as the "ΔΔ" mutation. The SYM5 and SYM6 core mutations have previously been described by us, and are designed to constrain the primary structure symmetry within the core to reflect the three-fold tertiary structure symmetry. The SYM5 mutant contains a total of five such core mutations, and the SYM6 mutant contains one additional mutation (see Table I). The Δ104-106, Δ120-122, and ΔΔ mutations were constructed within the background of both the SYM5 and SYM6 core mutations.

Mutagenesis and Expression.

All studies herein disclosed utilized a synthetic gene for the 140 amino acid form of human FGF-1 with the addition of an amino-terminal six residue "His-tag" to facilitate purification using nickel nitrilotriacetic acid (Ni-NTA) affinity resin (QIAGEN, Valencia Calif.). The QuikChange® site-directed mutagenesis protocol (Stratagene, La Jolla Calif.) was used to introduce mutations, individually or in combination, using mutagenic oligonucleotides of 25 to 31 bases in length (Biomolecular Analysis Synthesis and Sequencing Laboratory, Florida State University). For deletions involving residues 104-106 and 120-122, mutagenic oligonucleotides were used to delete these positions as well as to simultaneously create point mutations Ala103⟹Gly and Arg119⟹Gly, respectively. For the construction of the combination deletion mutants, the Δ104-106 mutation was introduced into the Δ120-122 mutant background (in either SYM5 or SYM6 parental constructs). All FGF-1 mutants were expressed using the pET21a(+) plasmid/BL21(DE3) *Escherichia coli* host expression system (Invitrogen Corp., Carlsbad Calif.). Mutant construction, expression and purification followed previously published procedures. Proteins containing the Δ120-122 mutation required substitution of Sephadex® G-50 size exclusion gel chromatography for the normally employed heparin Sepharose® affinity chromatography step, since this mutation was found deficient in heparin-binding functionality (see further discussion below).

Isothermal Equilibrium Denaturation.

Protein samples were equilibrated overnight in 20 mM N-2-(acetamido)iminodiacetic acid (ADA), 100 mM NaCl pH 6.60 at 298K in 0.1M increments of guanidine HCl (GuHCl). All samples contained a final protein concentration of 25 μM. An Aviv model 202 circular dichroism spectrometer (Proterion Corp., Piscataway, N.J.) equipped with a Peltier controlled temperature unit maintaining a constant temperature of 298K was used for all spectroscopic measurements. For each sample, triplicate scans were collected and averaged. Buffer traces were collected, averaged and subtracted from the sample traces. Data smoothing was performed prior to buffer subtraction using a 5-point Fourier transform filter. The denaturation process was monitored by observing the change in CD signal at 227 nm with increasing GuHCl, according to published references. The general purpose non-linear least squares fitting program DataFit™ (Oakdale Engineering, Oakdale Pa.) was used to fit the change in molar ellipticity at 227 nm versus GuHCl concentration to a six parameter two state model:

$$F = (F_{0N} + S_N[D] + F_{0D} + S_D[D]) e^{-((\Delta G0 + m[D])/RT)} / 1 + e^{-((\Delta G0 + m[D])/RT)} \quad (1)$$

where [D] is the denaturant concentration, $F_{0N}$ and $F_{0D}$ are the 0M denaturant molar ellipticity intercepts for the native and denatured states, respectively, and $S_N$ and $S_D$ are the slopes of the native and denatured state baselines, respectively. $\Delta G_0$ and m describe the linear function of the unfolding free energy versus denaturant concentration at 298K. The effect of a given mutation upon the stability of the protein (ΔΔG) was calculated by taking the difference between the $C_m$ values for WT* and mutant and multiplying by the average of the m values, as described by Pace and Scholtz (Measuring the conformational stability of a protein; in *Protein Structure: A Practical Approach*, Creighton, T. E., ed., pp. 299-321, Oxford University Press, Oxford; 1997):

$$\Delta\Delta G = (C_{m\,WT^*} - C_{m\,mutant})(m_{WT^*} + m_{mutant})/2 \quad (2)$$

Folding Kinetics Measurements.

Due to signal-to-noise considerations, relatively high protein concentrations (>100 μM) of FGF-1 were required for kinetic studies monitored by CD. At these concentrations protein precipitation occurred in ADA buffer. Therefore, a different buffering system was chosen for the kinetic studies to permit higher protein concentrations without precipitation. Protein samples were dialyzed against 50 mM sodium phosphate, 100 mM NaCl, 10 mM ammonium sulfate, 2 mM DTT, and typically 2.5, 3.0 or 3.8M GuHCl pH 7.5 overnight at 298K prior to data collection (higher concentrations of GuHCl were required to ensure complete denaturation for some stabilizing mutations).

Protein samples were degassed for 10 minutes prior to analysis. Refolding was initiated by a 1:10 dilution of protein solutions into 50 mM sodium phosphate, 100 mM NaCl, 10 mM ammonium sulfate, 2 mM DTT pH 7.5 containing either 0.1M or 0.05M increments of GuHCl up to the midpoint of denaturation. All data were collected using an Aviv model SF305 stopped flow system. Data collection times for each protein were designed to quantify the CD signal over 5 half-lives, or >96% of the total expected amplitude.

Unfolding Kinetics Measurements.

Protein samples (300 μM) were dialyzed against 50 mM sodium phosphate, 100 mM NaCl, 10 mM ammonium sulfate, 2 mM DTT pH 7.50 buffer overnight at 298K, and degassed for 10 min prior to data collection. Unfolding was initiated by 1:10 dilution of the native protein into 50 mM sodium phosphate, 100 mM NaCl, 10 mM ammonium sulfate, 2 mM DTT pH 7.5 buffer with final GuHCl concentration in the range of 1.5 to 5.5M in 0.5M increments. The unfolding process was quantified by following the change in CD signal at 227 nm, and data collection times for each protein were designed so as to monitor the CD signal over 3 to 4 half-lives, or >93% of the total expected amplitude.

Folding and Unfolding Kinetics Analysis.

Triplicate scans were collected for both folding and unfolding kinetic data at each GuHCl buffer condition. In all cases, data from at least three separate experiments were averaged. The kinetic rates and amplitudes versus denaturant concentration were calculated from the time dependent change in CD signal using a single exponential model:

$$I(t)=A\exp(-kt)+C \tag{3}$$

where I(t) is the intensity of CD signal at time t, A is the corresponding amplitude, k is the observed rate constant for the reaction and C is a constant that is the asymptote of the CD signal. Folding and unfolding rate constant data were fit to a global function describing the contribution of both rate constants to the observed kinetics as a function of denaturant ("Chevron" plot):

$$\ln(k_{obs})=\ln(k_{f0}\exp(m_{kf}D)+k_{u0}\exp(m_{ku}D)) \tag{5}$$

where $k_{f0}$ and $k_{u0}$ are the folding and unfolding rate constants, respectively, extrapolated to 0M denaturant, $m_{kf}$ and $m_{ku}$ are the slopes of the linear functions relating $\ln(k_f)$ and $\ln(k_u)$, respectively, to D, the denaturant concentration. Changes in activation barriers upon mutation were calculated using a modified version of transition state theory:

$$\Delta\Delta G_{\ddagger-D}=RT\ln(k_{fMut}/k_{fWT^*}) \text{ and } \Delta\Delta G_{\ddagger-N}=RT\ln(k_{uMut}/k_{uWT^*}) \tag{6}$$

where $k_{fMut}$, $k_{uMut}$, $k_{fWT^*}$ and $k_{uWT^*}$ are the folding and unfolding rates for mutant and WT*, respectively, in water. $\Delta\Delta G_{\ddagger-D}$, and $\Delta\Delta G_{\ddagger-N}$ are the changes in the activation barrier for folding and unfolding, respectively, between mutation and WT*. A positive value for $\Delta\Delta G_{\ddagger-D}$ or $\ddagger\ddagger G_{\ddagger-N}$ indicates a decrease in the associated activation barrier energy.

Isothermal Titration Calorimetry.

All ITC data were collected on a VP-ITC microcalorimeter (MicroCal LLC, Northampton Mass.). Titrations were performed at 298K and all samples were equilibrated in 20 mM ADA 100 mM NaCl pH 6.60 buffer. All samples were filtered and degassed for 10 minutes prior to loading. For WT* and SYM6ΔΔ, 20 μM and 47 μM protein concentrations were used with sucrose octasulfate concentrations of 400 μM and 930 μM, respectively. The samples were titrated against 40 injections, at 4 μL per injection, of sucrose octasulfate. Each injection was performed over an 8 second time frame, with a post injection equilibration period of 300 seconds. The titration curves were fit using the manufacturer's software (MicroCal Origin) employing a model with a single ligand binding site.

Cell Proliferation Assay.

NIH 3T3 fibroblasts were initially plated in Dulbecco's modified Eagle's medium (DMEM) (American Type Culture Collection, Manassas Va.) supplemented with 10% (v/v) newborn calf serum (NCS) (Sigma, St. Louis Mo.), 100 units of penicillin, 100 μg streptomycin, 0.25 μg Fungizone™ and 0.01 mg/ml gentamicin (Gibco, Carlsbad Calif.) ("serum-rich" medium) in T75 tissue culture flasks (Fisher, Pittsburgh Pa.). The cultures were incubated at 37° C. and all cell growth was performed with 5% $CO_2$ supplementation. At approximately 80% cell confluence, the cells were washed with 5 ml cold 0.14M NaCl, 5.1 mM KCl, 0.7 mM $Na_2HPO_4$ and 24.8 mM Trizma® base, pH 7.4 (TBS) and subsequently treated with 5 ml of a 0.025% trypsin solution (Invitrogen Corp., Carlsbad Calif.). Cell synchronization was initiated by serum starvation in DMEM with 0.5% NCS, 100 units of penicillin, 100 μg streptomycin, 0.25 μg Fungizone™ and 0.01 mg/ml gentamicin ("starvation" medium). The cells were seeded in T25 tissue culture flasks (Fisher, Pittsburgh, Pa.) at a cell density of $3.0\times10^4$ cells/cm$^2$ (representing ~20% confluence). Duplicate flasks were used for each protein concentration. Cultures were incubated for 48 hours at 37° C., the medium was then decanted and replaced with fresh medium supplemented with the appropriate concentration of FGF-1 polypeptide, and incubated for an additional 48 hours. After this incubation, the medium was decanted and the cells were washed with 1 ml cold TBS pH 7.4. 1 ml of 0.025% trypsin was then added to release the cells from the flask surface, and 2 ml of serum-rich medium were added to dilute and inhibit the trypsin. The cells were counted using a hemocytometer (Hausser Scientific Partnership, Horsham Pa.). Experiments were performed in quadruplicate and the cell densities were averaged. The relationship between the cell number and log concentration of added growth factor was fit to a sigmoidal function.

Results

Mutant Protein Production and Purification.

All mutant proteins, with the exception of the SYM6 mutant were expressed at levels similar to the WT* protein (i.e. ~30-100 mg/L). The SYM6 mutant exhibited a substantially reduced yield and a tendency to precipitate during purification. The His-tag provides the WT* and mutant FGF-1 proteins with nickel binding affinity, and FGF-1 naturally has a heparin binding site. These two affinity sites were employed in a purification scheme utilizing sequential nickel-NTA and heparin Sepharose® affinity chromatography resins. However, mutant forms of FGF-1 involving the Δ120-122 mutation lacked heparin-binding affinity. These mutants were, therefore, purified by the substitution of gel filtration chromatography for the heparin Sepharose® affinity chromatography. The extinction coefficients used for concentration determination were $E_{280nm}$ (0.1%, 1 cm)=1.26 for WT* and other mutations not involving deletions or the Leu44⟹Phe point mutation, $E_{280nm}$ (0.1%, 1 cm)=1.29 for non-deletion mutations involving Leu44⟹Phe, and $E_{280nm}$ (0.1%, 1 cm)=1.31 for all deletion mutations (determined by dithionitrobenzoate titration of cysteine residues).

Isothermal Equilibrium Thermodynamic Analysis.

Previous studies by others of the stability and folding of FGF-1 have been performed by monitoring the fluorescence signal of the single buried Trp 107 in FGF-1. This Trp in the WT* structure is somewhat unusual in that it is more highly quenched in the native state than the denatured. The Δ120-122 deletion mutant was observed to perturb the fluorescence quenching of Trp 107, thus, CD spectroscopy was utilized to monitor denaturation for all mutants. The structure of FGF-1 indicates that Trp 107 is quenched by Pro 121 in the native structure, and the deletion of Pro 121 diminishes this quenching. We have previously compared the fluorescence and CD spectroscopic response of FGF-1 to denaturation by GuHCl and shown essentially indistinguishable results for both his-tagged and non-his-tagged forms. A tabulation of the mutant thermodynamic data from isothermal equilibrium denaturation, monitored by CD signal, is listed in Table II. The data in this table for the SYM6 mutant are from our previously published isothermal equilibrium denaturation study monitored by fluorescence.

Folding and Unfolding Kinetics.

Due to the relatively weak differential CD signal of native and denatured FGF-1, the folding kinetics study required relatively high protein concentrations (>5 mg/ml). While readily soluble in high concentrations of GuHCl, subsequent rapid dilution into the lower GuHCl concentration regime resulted in precipitation for some mutant proteins (i.e. the least stable mutants). Thus, the refolding rate constants were not obtainable below certain denaturant concentrations for these mutants. In addition, the SYM6 mutant typically precipitated during concentration necessary for analysis, and we were unable to obtain any useful kinetic data for this mutant. The SYM6Δ120-122 mutant is substantially destabilized relative to the WT* protein (see Table II) and presents a relatively short "folding arm" in the Chevron plot, for this reason there is greater uncertainty associated with the folding kinetics determined for this mutant. Unfolding studies presented no problems associated with precipitation and exhibited single exponential kinetic properties for each mutant under all denaturant concentrations. Details of the folding and unfolding kinetics of WT* FGF-1 in GuHCl denaturant have previously been reported by us. WT* FGF-1 exhibits monoexponential folding behavior over a wide range of denaturant concentrations but deviates to bi-exponential folding behavior (exhibiting a "fast" and "slow" phase) under low denaturant concentrations (<~0.7M). The folding kinetics for all mutants, with the notable exception of SYM5ΔΔ and SYM6ΔΔ, followed similar folding behavior. The SYM5ΔΔ and SYM6ΔΔ, mutants exhibited single exponential folding behavior under all denaturant concentrations evaluated, and the combination of the loop mutations appear to have eliminated the slow-folding phase observed for WT* under low denaturant conditions. The folding and unfolding kinetic data are listed in Table III. We have previously reported folding and unfolding kinetic data for WT* monitored by fluorescence, and note that the data presented here for folding and unfolding, as monitored by CD signal, are in excellent agreement with the prior data.

Affinity for Sucrose Octasulfate Determined by Isothermal Titration Calorimetry.

FGF-1 mutants that included the Δ120-122 mutation exhibited a substantially reduced heparin binding affinity to the heparin Sepharose® chromatography matrix utilized in purification. To quantify the reduced affinity for heparin (a polysulfonated polysaccharide) we determined the affinity for sucrose octasulfate, a structural mimic of a heparin dimer, by isothermal titration calorimetry. As part of this evaluation, we compared both WT* and the SYM6ΔΔ mutant, which includes the Δ120-122 mutation. The thermodynamic binding parameters for these proteins are listed in Table IV.

Mitogenic Activity of WT* and Mutants of FGF-1.

Figure 3:
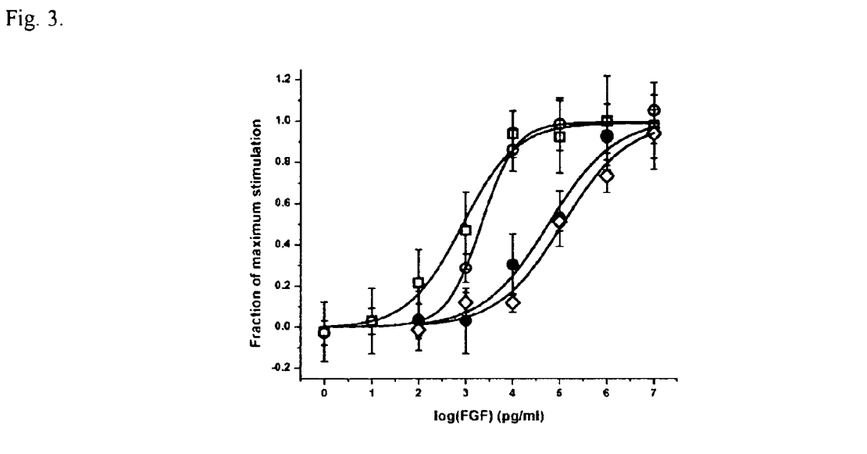
FIG. 3 depicts the results of mitogenic activity assay of WT* and mutant FGF-1 proteins against NIH 3T3 fibroblasts, wherein WT* (●), SYM5Δ104-106 (✴), SYM5Δ120-122 (○), and SYM6ΔΔ (□) mutants exhibit $EC_{50}$ values of 60, 115, 2.1, and 0.84 ng/ml, respectively; and where standard deviations of the measurements are indicated by the error bars.

Mitogenic activity towards NIH 3T3 fibroblasts was determined for WT*, SYM5, SYM5Δ104-106, SYM5Δ120-122, and SYM6ΔΔ mutants. These mutations are all either more stable or near-WT* in stability, and permit an evaluation of the effects of the loop deletion mutations upon mitogenic activity without concern for false-negatives due to instability effects. The NIH 3T3 fibroblast proliferative activity of WT* FGF-1 yielded an effective concentration for 50% maximal stimulation (EC50) of 60 ng/ml (FIG. 3). The SYM5 mutant showed essentially identical results as WT* (data not shown). The SYM5Δ104-106 mutant exhibited an EC50 of 115 ng/ml, or approximately two-fold less mitogenic activity in comparison to WT*. Surprisingly, the SYM6ΔΔ mutant exhibited an EC50 of 0.84 ng/ml, corresponding to an approximately 70 times increase in mitogenic activity in comparison to the WT* protein. The SYM5Δ120-122 mutant exhibited an EC50 of 2.1 ng/ml, an approximately 30-fold increase in mitogenic activity compared to WT*, suggesting that the increase in mitogenic activity observed for the SYM6ΔΔ mutant was primarily the consequence of the Δ120-122 mutation.

Discussion

In a previous study attempting to constrain the core region of FGF-1 to a symmetric primary structure, we found a highly conserved Met at position 67 to be essential for stability. Since the symmetry-related positions to Met 67 (positions 25 and 111, FIG. 1) comprised Ile and Leu side chains, respectively, the requirement for Met at position 67 was suspected to be due to a unique structural environment surrounding position 67. In particular, it was noted that two loop regions that pack against position 67 contain apparent insertions (i.e. residue positions 104-106 and 120-122) in comparison to the corresponding symmetry-related regions (FIG. 2). Furthermore, Met 67 adopts an alternate side chain $x_1$ angle (trans) in relationship to either Ile 25 or Leu 111 (which are both gauche+), and consequently orients its side chain towards the structural "aneurism" produced by the aforementioned insertions. Analysis of the FGF-1 structure indicated that an Ile or Leu substitution at position 67 (as is observed at the symmetry related positions 25 and 111, respectively) would result in a substantial cavity within the core region, adjacent to the loop insertions. Thus, it was theorized at that time that simple substitutions were insufficient to achieve a satisfactory alternative symmetric core-packing arrangement, and that modification of the tertiary structure (i.e. deletion of the insertions) would be required.

Another of our previous reports, studied the role of Gly residues in stabilizing type I β-turns, and investigated the deletion of residue positions 104-106 in FGF-1 and conversion of the local structure into a type I 4:6 β-turn. This publication identified an essential contribution to overall stability of a Gly residue at the i+3 position within type I β-turns. Thus, the 104-106 deletion by itself in the WT* structure resulted in a slight −1.5 kJ/mol increase in stability, but the subsequent Ala103⟹Gly mutation resulted in a further increase in stability of ~−6.0 kJ/mol. That study showed that design changes within a protein that result in the formation of a type I β-turn must take into account the nature of the residue at the i+3 position within the β-turn (and, in particular, ensure that it is a Gly residue). Using the symmetry-related positions within FGF-1 as a structural guide, the deletion of residue positions 120-122 was similarly postulated to result in the formation of an adjacent β-hairpin turn (involving residue positions 116-119). Residue 119 would correspond to the i+3 position in the nascent β-turn. A comparison of the symmetry-related residues to this position (i.e. positions 33 and 75) demonstrated conserved Gly residues in each case (FIG. 1). Thus, the 120-122 deletion was combined with an Arg119⟹Gly mutation in an approach similar to that taken with the 104-106 deletion mutation.

Figure 4:
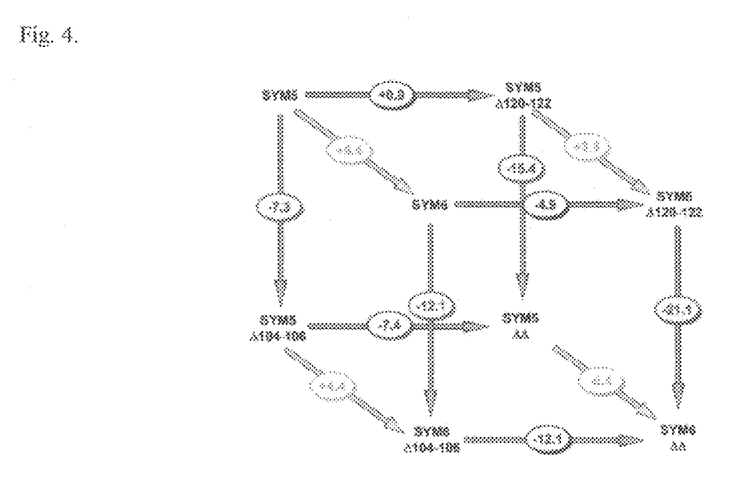
FIG. 4 is a graphical representation of the effects upon stability for the individual Δ104-106, Δ120-122 and SYM5⟹SYM6 (i.e. Met67⟹Ile) mutations when constructed in different background forms of FGF-1; red arrows indicate the effect of the Δ104-106 mutation, blue arrows indicate the effect of the Δ120-122 mutation, and green arrows indicate the effect of the Met67⟹Ile mutation (i.e. SYM5⟹SYM6); the ΔΔG values (kJ/mol) for the mutagenic steps are provided, where a negative value indicates the mutation is stabilizing.
Figure 5:
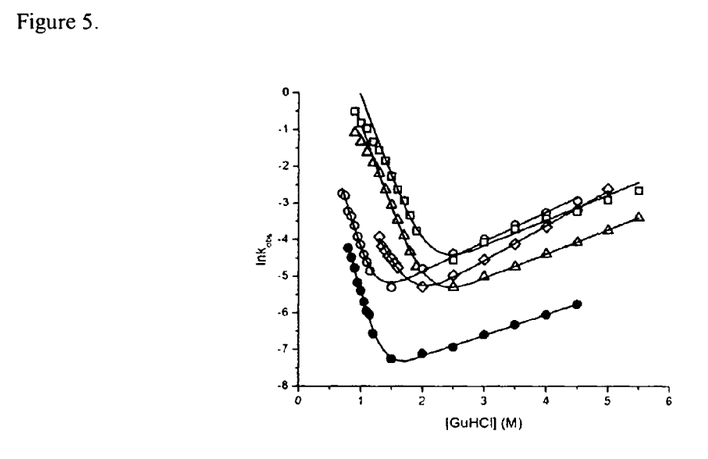
FIG. 5 shows folding and unfolding rate constants as a function of GuHCl denaturant (i.e. "Chevron plots") for SYM5 mutants and demonstrates the effects of the loop deletions and position 67 substitution; the various polypeptides are represented as follows, SYM5 (●), SYM5Δ104-106 (✴), SYM5Δ120-122 (○), SYM5ΔΔ(▲), and SYM6ΔΔ (□) mutants.

A convenient illustration, representing a series of "double-mutant cycles," of the stability consequences of the combination of each of the two loop deletions and the position 67 substitution mutation is shown in FIG. 4. If we start with SYM5 and introduce the Δ104-106 deletion mutant (i.e. the red arrows in FIG. 4), it results in a −7.3 kJ/mol increase in stability (essentially identical to the results in the WT* protein). However, if the Δ120-122 deletion mutation is first introduced into SYM5, the Δ104-106 deletion mutant is now observed to increase the stability by −15.4 kJ/mol. Similarly, if position 67 has already been mutated to Ile (to convert SYM5 to SYM6), the Δ104-106 deletion mutant is now observed to increase the stability by −12.1 kJ/mol. Finally, if both the Δ120-122 deletion mutation and the position 67 Ile mutation have already been introduced (i.e. SYM6Δ120-122 as the background protein), the Δ104-106 deletion mutant is now observed to increase the stability by −21.1 kJ/mol.

When considering the effects of the Δ120-122 deletion mutation (the blue arrows in FIG. 4), unlike the Δ104-106 deletion mutation, the Δ120-122 deletion mutation is not stabilizing when introduced into the SYM5 protein (it exhibits a slight destabilization of +0.9 kJ/mol). However, if the Δ104-106 deletion mutation has already been introduced into SYM5, the Δ120-122 deletion mutant is now observed to increase the stability by −7.4 kJ/mol.

Similarly, if position 67 has already been mutated to Ile (i.e. SYM6 as the background protein), the Δ120-122 deletion mutant is now observed to increase the stability by −4.9 kJ/mol. Finally, if both the Δ104-106 deletion mutation and the position 67 Ile mutation have already been introduced (i.e. SYM6Δ104-106 as the background protein), the Δ120-122 deletion mutant is now observed to increase the stability by −12.1 kJ/mol.

When considering the effects of the Met67⟹Ile mutation (the green arrows in FIG. 4), as previously reported, the Met67⟹Ile mutation destabilizes the SYM5 protein by +9.4 kJ/mol 19. However, if the Δ104-106 deletion mutation has already been introduced into SYM5, the Met67⟹Ile mutation destabilizes the structure by only +4.4 kJ/mol. Similarly, if the Δ120-122 deletion mutation has already been introduced into SYM5, the Met67⟹Ile mutation destabilizes the structure by only +3.8 kJ/mol. Finally, if both the Δ104-106 and Δ120-122 deletion mutations have already been introduced (i.e. SYM5ΔΔ as the background protein), the Met67⟹Ile mutation is now observed to actually increase the stability by a modest −0.4 kJ/mol. The effect of combining the two loop deletions is that the Met residue at position 67 is no longer required for stability (i.e. mutation by Ile is essentially a neutral substitution).

The above analyses indicate a high degree of cooperativity between the two loop deletion mutations and the position 67 substitution. If one considers the SYM5ΔΔ protein as a starting frame of reference, the simple sum for the insertion of both loop regions (producing the SYM5 protein) would predict a destabilizing effect of +22.8 kJ/mol, however, the resulting effect on stability is only +15.0 kJ/mol. Similarly, if one considers a related analysis for the SYM6ΔΔ protein, the simple sum of the two loop insertions would predict a destabilizing effect of +33.2 kJ/mol when producing the SYM6 protein, however, the actual effect on stability is +25.3 kJ/mol. Thus, not only is the Met 67 residue helping to mitigate the destabilizing effects of both loop insertions, the loops themselves are interacting to minimize destabilization. A simple sum of the individual mutational effects predicts that, if starting with SYM5, the SYM5ΔΔ combination mutant should be destabilizing by +3.0 kJ/mol (−7.3+0.9+9.4), whereas, the actual combination mutant is −15.1 kJ/mol more stable than the SYM5 protein. Thus, the three structural elements have co-evolved to optimize the stability of their interactions. However, despite these cooperative interactions, the deletion of both loop insertions results in a substantial increase in protein stability of approximately −15 kJ/mol. Thus, regardless of the cooperativity, the protein would be far more stable without these insertions. A reduction in loop length is expected to stabilize the structure due to entropic considerations. The turns at the symmetry-related positions to residues 104-106 are both type I 4:6 turns (i.e. four residues within the turn), whereas, the turns at the symmetry-related positions to residues 120-122 are both type I 3:5 turns (i.e. three residues within the turn). The expected stability gain from entropic considerations would therefore be approximately −1.5 kJ/mol (for a 7 residue to 4 residue loop conversion) and −2.5 kJ/mol (for a 6 residue to 3 residue loop conversion) based upon the loop insertion study of Nagi and Regan (*Fold Des* 2, 67-75; 1997). Thus, the approximately −15 kJ/mol increase in stability for the combined loop deletions appears to be primarily enthalpically driven, and represents optimization of non-covalent interactions within the turns and adjacent secondary structure. The stability/function trade-off hypothesis would suggest that functional considerations may be associated with the substantial stability penalty associated with adopting the loop insertions. The lack of affinity for heparin Sepharose® by FGF-1 mutants that include the Δ120-122 mutation demonstrates that heparin-binding functionality is contributed by this region. The ITC study of binding to sucrose octasulfate indicates that the binding affinity to this heparin dimer analogue is diminished by an order of magnitude, although it is not completely eliminated (Table IV).

Structural and biochemical studies of FGFs have previously identified a key role for heparin in forming a functional signal transduction complex of FGF with its receptor (FGFR). Thus, in the present study it came as an unexpected surprise to find that the SYM6ΔΔ mutant exhibits an EC50 value that is almost two orders of magnitude more potent in comparison to WT* FGF-1, see FIG. 3. A comparison with other FGF-1 mutants involving only a single loop deletion indicates that this increase in potency is associated with the Δ120-122 mutation.

This unexpected finding raises the question of why should the diminution of affinity for heparin increase the apparent potency of FGF-1? Without wishing to be bound thereto, the inventors theorize that one possibility is a "free concentration" effect. That is, typically the majority of FGF-1 added to cells in culture may be sequestered by heparan proteoglycan on the cell surface and may not be directly available for binding to the receptor. However, it may be that the Δ120-122 mutation would not be effectively sequestered by heparan proteoglycan (judging from the behavior on heparin Sepharose) and that the effective free concentration of the FGF polypeptide may, therefore, be substantially higher than an equivalent concentration of added WT*.

The residual heparin-binding affinity (as shown by the ITC data) appears sufficient for formation of an effective FGF/FGFR/heparin signaling complex. Thus, the in vivo functionality associated with the loop 120-122 region may be related to sequestering or storage of FGF-1 in heparan proteoglycan on the cell surface, or heparin in the extracellular matrix, rather than to formation of the signaling complex. Such a stored form of FGF-1 could be released during subsequent degradation of the extracellular matrix, as in wound formation or tissue remodeling.

The loop 104-106 does not appear to be directly related to heparin binding, and its deletion has been shown here to have little effect upon mitogenic activity, see FIG. 3. Thus, the loop 104-106 insertion, along with the Met 67 residue, may be a mutational response to accommodate the instability associated with the heparin-binding functionality afforded by the insertion of residues 120-122. The SYM6ΔΔ mutant exhibits greater mitogenic activity than the sum of the effects of the individual loop deletion mutations exhibited within the SYM5 background. Since cooperative effects upon stability are observed for the loop deletions in combination with the position 67 substitution, this may contribute to the observed non-additive increase in mitogenicity via a stability-based mechanism.

The relationship between the folding and unfolding rate constants with denaturant concentration (i.e. "Chevron plot") for the SYM5 loop mutations is shown in FIG. 5. These results illustrate that either loop deletion results in both faster folding and unfolding rates for the mutant FGF-1 protein (in the case of the Δ104-106 deletion, however, the rate of unfolding is increased to a much greater extent than the rate of folding, the net result being an overall destabilization of the protein). This generalized vertical shift of the "Chevron plot" is indicative of a stabilization of the folding transition state ensemble (TSE), see Table III. Thus, the organization of the local structure involving loops 104-106, 120-122 and Met67 has a key (unfavorable) influence upon the energetics of the TSE in the WT* protein. The observed changes in the energy barrier associated with the TSE (i.e. $\Delta\Delta G_{\ddagger\text{-}D}$ and $\Delta\Delta G_{\ddagger\text{-}N}$; see Table III) highlights the cooperativity between position 67 and the 104-106 and 120-122 loop regions. Furthermore, the present results also identify a specific contribution of the Met residue at position 67 in destabilizing the TSE. When comparing the SYM5 loop deletion mutants (containing Met67) with the SYM6 loop deletion mutations (containing Ile67), the Met67 substantially decreases the folding and unfolding rate (Table III).

It has been previously reported that FGF-1 and other members of the FGF family of proteins are unusual in that they have no identifiable secretion signal and are secreted in an endoplasmic reticulum-independent manner. FGF-1 is known to have generally low thermal stability, and a partially-folded form (i.e. kinetically-trapped intermediate) of FGF has been postulated to be able to directly insert and translocate across the lipid bilayer. The influence on the energetics of the TSE by the 104-106 region, 120-122 region, and Met67, indicates that they may contribute a functional role in the unusual secretion mechanism of FGF-1. In this regard we theorize, without wishing to be bound thereto, that the SYM6ΔΔ mutant in vivo may exhibit an impaired ability to translocate across lipid bilayers and therefore, might not be secreted if expressed within cells. The present results also highlight the influence that specific turn regions can exert upon the TSE energetics and, therefore, to the overall folding and unfolding kinetics of a protein.

The SYM5 mutant was previously constructed by others to test the hypothesis that the core of a symmetric superfold could be effectively redesigned with a symmetric primary structure constraint. This design goal achieved a measure of success, but reached an apparent impasse when attempting to mutate a highly-conserved Met at position 67. The solution to this impasse, we believed, would be to require adjustments to the tertiary structure, involving deletions of two apparent structural insertions. Thus, the goal of increasing the primary structure symmetry was found to be linked to a concomitant increase in the tertiary structure symmetry. The presently described deletion of regions 104-106 and 120-122 has eliminated the structural requirement of Met at position 67, and an Ile mutation at this position can now be accommodated. Thus, the core region in the SYM6ΔΔ mutant comprises a total of four triplets of identical residue positions related by the three-fold structural symmetry: Leu at positions 23, 65, and 109; Ile at positions 25, 67 and 111; Val at positions 31, 73, and 117; and Phe at positions 44, 85, and 132. There remains a single triplet region within the core to constrain to three-fold symmetry, involving residues Leu 14, Ile 56 and Tyr 97. By deleting these loop regions we have also increased the tertiary structure symmetry of FGF-1.

In the FGF-1 structure each trefoil subdomain is a different length. The combined loop deletion (i.e. ΔΔ) mutants result in trefoil subdomains 2 and 3 being exactly 41 amino acids in length, while the first domain remains 42 amino acids in length (ignoring the details of the flexible amino terminus residues). Thus, there remains a modification of the first trefoil domain to produce a completely symmetric tertiary structure.

In addition to the above described core positions constrained to three-fold symmetry, the substitution of the two Gly residues at positions 103 and 119 results in the symmetry-related residues at positions 20, 62 and 103, and 33, 75 and 119, being constrained to the same residue (Gly). Therefore, while WT* FGF-1 exhibits only a single triplet (positions 29, 71, and 115) with identical residues (Gly), the SYM6ΔΔ mutant has six additional positions. As noted, this symmetric-constraint redesign of FGF-1 has been accomplished with an ~16 kJ/mol increase in stability in comparison to WT*. Although this increase in stability was unexpected, it has led us to propose the hypothesis that a primary structure symmetric constraint, within a symmetric protein superfold, might represent a solution to, rather than constraint upon, the stability and foldability of the polypeptide. We are pursuing additional core and turn mutations to increase the primary and tertiary structure symmetry of FGF-1 to test this hypothesis further.

The Invention in Use

The presently described invention comprises several mutant polypeptides having altered biological functionalities which include altered binding affinity for heparin, altered mitogenic potency, and combinations thereof.

Unexpectedly, the mutant polypeptide described herein and designated SYM6ΔΔ demonstrated decreased heparin binding affinity and approximately a 70 times increase in mitogenicity when compared to the wild type polypeptide. The SYM6ΔΔ is shown in SEQ ID NO: 1. In addition, the mutant designated SYM5Δ120-122 also demonstrated significantly increased mitogenic activity over the wild type polypeptide, approximately a 30-fold increase in activity. SYM5Δ120-122 is shown in SEQ ID NO: 2. Furthermore, the data presented herein predict that deletion of the residues at positions 120-122 will produce a polypeptide having decreased heparin binding affinity and increased biological activity with regard to mitogenicity. Accordingly, the wild type polypeptide with a deletion at positions 120-122 has been designated WTΔ120-122 and is shown in SEQ ID NO: 3. The wild type polypeptide of FGF-1, as previously described by others, is shown in SEQ ID NO: 4.

Those skilled in the art will readily recognize that a mutant FGF-1 polypeptide having increased mitogenic activity may be advantageously employed in any application wherein rapid proliferation of tissue and cells is desirable, whether in vitro or in vivo. For example, the presently disclosed mutant polypeptides could be used in tissue engineering for rapidly propagating cultured cells to form tissue which may then be harvested for further uses such as tissue transplants. Additionally, the present mutant polypeptides may be applied in vivo to damaged tissue(s) in order to stimulate cell proliferation leading to tissue repair. For use in vivo, the mutant polypeptide(s) may be combined in a pharmaceutically acceptable composition suitable for the task. Furthermore, the mutant polypeptides and pharmaceutical compositions thereof may be combined with a medical device for treatment of biological tissues. For example, an adhesive bandage may bear an amount of the mutant polypeptide and/or a pharmaceutical composition thereof, so that when the bandage is applied to damaged skin or other tissue, the mutant polypeptide will aid in healing by stimulating cell growth. A surgical instrument could be coated with an amount of one or more of the present polypeptides, so as to deposit the stimulating polypeptide on a patient's tissues during use of the instrument. Other examples of medical devices bearing the mutant polypeptide of the invention include suture material, gauze for bandages, and endoscopic instruments. Yet additionally, a biocompatible tissue glue such as used as an alternative to sutures could contain one of the mutant polypeptides of the present invention to promote healing of the adhered tissues.

The present invention, therefore, discloses a purified polypeptide, the amino acid sequence of which consists essentially of SEQ ID NO: 1. The invention also discloses a method of treating a biological tissue, the method comprising contacting the tissue with the polypeptide of SEQ ID NO: 1 or with the polypeptide comprising at least one conservative amino acid substitution. The method of treating a biological tissue comprises contacting the tissue with a pharmaceutical composition containing the polypeptide of SEQ ID NO: 1 or containing the polypeptide comprising at least one conservative amino acid substitution. The invention further includes a method of treating a biological tissue by contacting the tissue with a medical device bearing the polypeptide of SEQ ID NO: 1 or SEQ ID NO: 1 comprising at least one conservative amino acid substitution. Alternatively, a method of treating a biological tissue may comprise contacting the tissue with a medical device bearing a composition containing the polypeptide of SEQ ID NO: 1 or SEQ ID NO: 1 having at least one conservative amino acid substitution.

The invention additionally includes a purified polypeptide having relatively low heparin binding affinity, the amino acid sequence of which is selected from a sequence consisting essentially of SEQ ID NO: 1, SEQ ID NO: 2, SEQ ID NO: 3, and combinations thereof. Alternatively, this described polypeptide includes at least one conservative amino acid substitution. Moreover, a method of treating a biological tissue includes contacting the tissue with this polypeptide or polypeptide combination, including wherein the polypeptide or combination contains a conservative amino acid substitution. This method of treating a biological tissue may comprise contacting the tissue with a pharmaceutical composition containing the polypeptide or the polypeptide or combination of polypeptides containing at least one conservative amino acid substitution. As previously noted, this method of treating a biological tissue may comprise contacting the tissue with a medical device bearing the polypeptide of SEQ ID NO: 1, SEQ ID NO: 2, SEQ ID NO: 3, and combinations thereof, and which may include at least one conservative amino acid substitution. Furthermore, the method of treating a biological tissue may comprise contacting the tissue with a medical device bearing a composition containing the polypeptide as described.

Accordingly, in the drawings and specification there have been disclosed typical preferred embodiments of the invention and, although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as recited in the appended claims.

TABLE I

Nomenclature for mutant forms of FGF-1.

| Acronym | Mutations |
|---|---|
| WT* | Wild type (his-tagged) |
| SYM5 | Leu44→Phe/Leu73→Val/Val109→Leu/Leu111→Ile/Cys117→Val |
| SYM6 | Leu44→Phe/Met67→Ile/Leu73→Val/Val109→Leu/Leu111→Ile/Cys117→Val |
| Δ104-106 | Ala103→Gly/ΔGlu104/ΔLys105/ΔAsn106 |
| Δ120-122 | Arg119→Gly/ΔGly120/ΔPro121/ΔArg122 |
| ΔΔ | Δ104-106/Δ120-122 |

TABLE II

Thermodynamic parameters for WT* and mutant FGF-1 proteins as determined by isothermal equilibrium denaturation in guanidine HCl and monitored by CD signal at 227 nm.

| Protein | $\Delta G_0$ (kJ/mol) | m-value (kJ/mol M) | $C_m$ (M) | $\Delta\Delta G^a$ (kJ/mol) |
|---|---|---|---|---|
| WT* | 21.3 ± 0.8 | 20.1 ± 0.5 | 1.06 ± 0.01 | 0.0 |
| SYM5 | 18.4 ± 0.4 | 17.5 ± 0.3 | 1.05 ± 0.01 | 0.2 |
| SYM5/Δ104-106 | 25.3 ± 0.9 | 17.2 ± 0.5 | 1.47 ± 0.01 | −7.6 |
| SYM5/Δ120-122 | 16.6 ± 0.5 | 16.6 ± 0.5 | 1.00 ± 0.02 | 1.1 |
| SYM5/ΔΔ | 34.2 ± 1.2 | 18.1 ± 0.7 | 1.89 ± 0.01 | −15.9 |
| SYM6[b] | 10.4 ± 0.8 | 19.3 ± 1.9 | 0.54 ± 0.01 | 10.2 |
| SYM6/Δ104-106 | 20.5 ± 0.5 | 16.9 ± 0.5 | 1.21 ± 0.01 | −2.8 |
| SYM6/Δ120-122 | 15.7 ± 0.2 | 20.0 ± 0.2 | 0.79 ± 0.01 | 5.4 |
| SYM6/ΔΔ | 33.9 ± 0.6 | 17.7 ± 0.4 | 1.91 ± 0.02 | −16.1 |

[a] $\Delta\Delta G = (C_{m\ WT^*} - C_{m\ mutant})^*(m_{WT^*} + m_{mutant})/2$ as described by Pace [29]. A negative value indicates a more stable mutation in relationship to the wild type protein. All errors are stated as standard error from multiple data sets.
[b] Previously reported isothermal equilibrium data monitored by fluorescence signal [19].

TABLE III

Folding and unfolding kinetic parameters for WT* and mutant FGF-1 proteins derived from the global ("Chevron plot") fit using guanidine hydrochloride as the denaturant.

| Protein | $k_f$ (sec$^{-1}$) | $m_f$ (M$^{-1}$) | $k_u$ (1 × 10$^{-3}$ sec$^{-1}$) | $m_u$ (M$^{-1}$) | $\Delta\Delta G_{\ddagger\text{-}D}$ (kJ/mol)[b] | $\Delta\Delta G_{\ddagger\text{-}N}$ (kJ/mol)[b] |
|---|---|---|---|---|---|---|
| WT* | 3.31 | −6.05 | 0.69 | 0.47 | 0 | 0 |
| SYM5 | 2.57 | −6.44 | 0.25 | 0.57 | −0.63 | −2.51 |
| SYM5/Δ104-106 | 2.00 | −3.70 | 0.62 | 0.95 | −1.25 | −0.25 |
| SYM5/Δ120-122 | 7.29 | −6.44 | 1.60 | 0.80 | 1.96 | 2.10 |
| SYM5/ΔΔ | 40.4 | −4.57 | 0.88 | 0.66 | 6.20 | 0.61 |
| SYM6[a] | — | — | — | — | — | — |
| SYM6/Δ104-106 | 30.1 | −5.41 | 3.33 | 0.94 | 5.47 | 3.91 |

TABLE III-continued

Folding and unfolding kinetic parameters for WT* and mutant FGF-1 proteins derived from the global ("Chevron plot") fit using guanidine hydrochloride as the denaturant.

| Protein | $k_f$ (sec$^{-1}$) | $m_f$ (M$^{-1}$) | $k_u$ ($1 \times 10^{-3}$ sec$^{-1}$) | $m_u$ (M$^{-1}$) | $\Delta\Delta G_{\ddagger\text{-}D}$ (kJ/mol)[b] | $\Delta\Delta G_{\ddagger\text{-}N}$ (kJ/mol)[b] |
|---|---|---|---|---|---|---|
| SYM6/Δ120-122 | 17.3 | −9.45 | 7.95 | 0.86 | 4.10 | 6.07 |
| SYM6/ΔΔ | 74.0 | −4.40 | 1.90 | 0.69 | 7.70 | 2.52 |

[a]Low protein solubility prevents accurate analysis.
[b]Calculated in reference to the WT* protein; a positive value indicates a decrease in the associated activation barrier energy.

TABLE IV

Thermodynamic binding parameters for WT* and SYM6/ΔΔ mutant FGF-1 to sucrose octasulfate as determined by isothermal titration calorimetry.

| Protein | Stoichiometry (n) | $K_d$ (M) | ΔH (kJ/mol) |
|---|---|---|---|
| WT* | 1.22 ± 0.03 | 3.5 ± 0.3 | −6.7 ± 0.3 |
| SYM6/ΔΔ | 1.00 ± 0.09 | 40.6 ± 2.5 | −8.9 ± 1.2 |

That which is claimed:

1. A method of stimulating mitogenesis in cells by contacting same with a purified polypeptide of mutated human fibroblast growth factor 1, the amino acid sequence of which consists essentially of SEQ ID NO: 1.

2. The method of claim 1, wherein said polypeptide is contained in a pharmaceutical composition.

3. The method of claim 1, wherein said polypeptide contacts said cells by being delivered from a medical device.

4. The method of claim 3, wherein said polypeptide is contained in a pharmaceutical composition.

5. A medical device bearing the purified polypeptide consisting essentially of SEQ ID NO: 1 and adapted for delivering said polypeptide into contact with cells or tissues.

6. A method of treating a damaged biological tissue in vivo to stimulate proliferation cells leading to tissue repair, the method comprising contacting said tissue with an isolated mutant polypeptide of FGF-1, the amino acid sequence of which consists essentially of SEQ ID NO:1.

7. A method of treating cells to stimulate cell proliferation, the method comprising contacting the cells with a purified polypeptide the amino acid sequence of which is selected from a sequence consisting essentially of SEQ ID NO: 2 or SEQ ID NO: 3.

* * * * *

SEQUENCE LISTING

<160> NUMBER OF SEQ ID NOS: 4

<210> SEQ ID NO 1
<211> LENGTH: 134
<212> TYPE: PRT
<213> ORGANISM: Human FGF-1 mutant SYM6DD

<400> SEQUENCE: 1

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Ile Asp Thr Asp Gly Leu Val Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Gly Trp Phe Leu Gly Ile Lys Lys Asn Gly
            100                 105                 110

Ser Val Lys Gly Thr His Tyr Gly Gln Lys Ala Ile Leu Phe Leu Pro
        115                 120                 125

Leu Pro Val Ser Ser Asp
    130
```

<210> SEQ ID NO 2
<211> LENGTH: 137
<212> TYPE: PRT
<213> ORGANISM: Human FGF-1 mutant SYM5D120-122

<400> SEQUENCE: 2

```
Phe Asn Leu Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
            35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Val Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Leu Gly Ile Lys
               100                 105                 110

Lys Asn Gly Ser Val Lys Gly Thr His Tyr Gly Gln Lys Ala Ile Leu
           115                 120                 125

Phe Leu Pro Leu Pro Val Ser Ser Asp
           130                 135

<210> SEQ ID NO 3
<211> LENGTH: 137
<212> TYPE: PRT
<213> ORGANISM: Human FGF-1 mutant WTD120-122

<400> SEQUENCE: 3

Phe Asn Leu Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
               100                 105                 110

Lys Asn Gly Ser Cys Lys Gly Thr His Tyr Gly Gln Lys Ala Ile Leu
           115                 120                 125

Phe Leu Pro Leu Pro Val Ser Ser Asp
           130                 135

<210> SEQ ID NO 4
<211> LENGTH: 140
<212> TYPE: PRT
<213> ORGANISM: Human FGF-1 wild type

<400> SEQUENCE: 4

Phe Asn Leu Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
            35                  40                  45
```

-continued

```
Glu Ser Val Gly Glu Val Tyr Ile Lys Ser Thr Glu Thr Gly Gln Tyr
    50              55              60

Leu Ala Met Asp Thr Asp Gly Leu Leu Tyr Gly Ser Gln Thr Pro Asn
65              70              75              80

Glu Glu Cys Leu Phe Leu Glu Arg Leu Glu Glu Asn His Tyr Asn Thr
            85              90              95

Tyr Ile Ser Lys Lys His Ala Glu Lys Asn Trp Phe Val Gly Leu Lys
            100             105             110

Lys Asn Gly Ser Cys Lys Arg Gly Pro Arg Thr His Tyr Gly Gln Lys
        115             120             125

Ala Ile Leu Phe Leu Pro Leu Pro Val Ser Ser Asp
    130             135             140
```